US008310672B2

(12) United States Patent
Schmidt et al.

(10) Patent No.: US 8,310,672 B2
(45) Date of Patent: Nov. 13, 2012

(54) METHOD FOR GENERATING AND FOR DETECTING A RAMAN SPECTRUM

(75) Inventors: Heinar Schmidt, Berlin (DE); Daniel Pérez Kaiser, Berlin (DE); Martin Maiwald, Berlin (DE)

(73) Assignee: Forschungsverbund Berlin E.V., Berlin (DE)

( * ) Notice: Subject to any disclaimer, the term of this patent is extended or adjusted under 35 U.S.C. 154(b) by 0 days.

(21) Appl. No.: 13/413,355

(22) Filed: Mar. 6, 2012

(65) Prior Publication Data

US 2012/0162641 A1    Jun. 28, 2012

Related U.S. Application Data

(63) Continuation of application No. PCT/EP2010/063606, filed on Sep. 16, 2010.

(30) Foreign Application Priority Data

Sep. 21, 2009    (DE) .......................... 10 2009 029 648

(51) Int. Cl.
*G01J 3/44* (2006.01)
(52) U.S. Cl. ....................................................... 356/301
(58) Field of Classification Search .............. 356/72–73, 356/301
See application file for complete search history.

(56) References Cited

U.S. PATENT DOCUMENTS 7,760,352 B2 * 7/2010 Armstrong et al. ........... 356/301
2005/0254047 A1 11/2005 Brady

FOREIGN PATENT DOCUMENTS

WO    2006/130728 A2    12/2006

OTHER PUBLICATIONS

Shreve Apetal: "Effective Rejection of Fluorescence Interferencein Raman Spectroscopy Using a Shifted Excitation Difference Technique", Applied Spectroscopy, Bd. 46, Nr. 4, Apr. 1, 1992, p. 707-711, XP000264023.
McCain S T etal: "Multi-excitation Raman spectroscopy technique for fluorescence rejection", Optics Express, Bd. 16 Nr. 15, 2γ. May 2008, p. 10975-10991 , XP002615262.
Maiwald M et al: "Rapid shifted excitation Raman difference spectroscopy with a distributed feedback diode laser emitting at 785 nm", Applied Physics B; Lasers and Optics, Springer, Berlin, DE, Bd. 85, Nr. 4, Sep. 20, 2006, p. 509512, XP019459658.

* cited by examiner

Primary Examiner — Tariifur Chowdhury
Assistant Examiner — Abdullah Nur
(74) Attorney, Agent, or Firm — Perkins Coie LLP; Aaron Wininger (57) ABSTRACT

A method and a device for generating and for detecting a Raman spectrum enables an automated, or automatable, and at the same time quantitative SERD spectroscopy (for example concentration measurement series). To this end, during the SERD spectroscopy, a first spectrum and a second spectrum are standardized in relation to one another in terms of intensity values and a first difference spectrum is subsequently calculated, a second difference spectrum is calculated, the first difference spectrum is converted into a first transformation spectrum, the second difference spectrum is converted into a second transformation spectrum, and the Raman spectrum is calculated by adding the first transformation spectrum and the second transformation spectrum.

23 Claims, 5 Drawing Sheets

Fig. 10

METHOD FOR GENERATING AND FOR DETECTING A RAMAN SPECTRUM

PRIORITY CLAIM

This application is a continuation of Patent Cooperation Treaty Application No. PCT/EP2010/063606 filed Sep. 16, 2010, which claims priority to German Patent Application No. 10 2009 029 648.4 filed Sep. 21, 2009, both of which are incorporated by reference.

TECHNICAL FIELD

The present invention relates to a method and to a device for generating and for detecting a Raman spectrum.

BACKGROUND

On account of its suitability for in-situ and on-line chemical analysis, Raman spectroscopy is increasingly being used in industrial process engineering and environmental metrology, wherein a disadvantage includes the fact that in practice the fluorescence and/or the scattering properties of some samples result in the generation of spectra whose quality is affected by a high background, particularly if the samples are not prepared and compact equipment is used.

One approach to solving this problem is the technique of shifted-excitation Raman difference spectroscopy (also referred to as "SERDS" in the following), wherein two Raman spectra whose excitation wavelengths are slightly shifted with respect to each other are recorded. The broadband background is eliminated by subtraction, and the Raman spectrum is reconstructed from the difference spectrum.

Tuning the excitation wavelength by means of the temperature has been a usual method since diode lasers were made available, wherein the temperature is typically controlled and stabilized thermoelectrically. The change in temperature enables the emission wavelength to be shifted by some nanometers (J. Zhao, M. M. Carraba, and F. S. Allen, Appl. Spectrosc. 56, 834 (2002)).

However, the wavelength stability of simple Fabry-Perot diode lasers is not sufficient for performing Raman spectroscopy so that additional stabilization is necessary therefor. For example, external-cavity semiconductor lasers (ECL lasers) enable the frequency to be shifted by turning the outer grating (T. F. Cooney, H. T. Skinner and S. M. Angel in Appl. Spectrosc., Vol. 49 (1995), pp 1846-1851).

If no tunable laser source is available, the majority of dispersive spectrometers provide the possibility of turning the grating by a small angle, whereby the spectrum spectrally shifts together with the background by the amount Δ (Steven E. J. Bell, Elsa S. O. Bourguignon and Andrew Dennis, Analyst, Vol. 123 (1729-1734) (1998)).

From WO 2006/134103 A1 and M. Maiwald, G. Erbert, A. Klehr, H. -D. Kronfeldt, H. Schmidt, B. Sumpf and G. Tränkle, Appl. Phys. B 85, 509-512 (2006) it is known to directly modulate the wavelength of a DFB laser by means of the injection current of the DFB laser. Being driven at 785 nm at two different amperages causes the frequency-stable DFB diode laser to accordingly emit at two different wavelengths. The main advantage includes the possibility of quickly switching between two wavelengths, wherein no movable parts are required. Thus, this method is cut out for fast on-line chemical analysis.

WO 2006/130728 A2 discloses a method for generating and detecting a Raman spectrum of a medium to be analyzed, wherein a difference spectrum is calculated by subtraction of the first spectrum and the second spectrum.

Various algorithms for reconstructing a Raman spectrum from a difference spectrum are known in the prior art.

Shreve et al. (R. A. Mathies, A. P. Shreve, N. J. Cherepy, Appl. Spectrosc. 46, 707 (1992)) describe a manual fit of Lorentz functions to the difference spectrum according to the method of least error squares. However, this modeling requires previous knowledge of the original spectrum as well as a check by a user, which is why this technique cannot be automated.

Since SERD spectra are similar to first-order derivative spectra, integration thereof is obvious. This process can be automated but results in the formation of artifacts so that manual finishing work is necessary.

Matousek et al. describe a linear recursive algorithm with linear interpolation between the data points (P. Matousek, M. Towrie, and A. W. Parker, "Simple reconstruction algorithm for shifted excitation Raman difference spectroscopy," Applied Spectroscopy, vol. 59, 2006). This algorithm can be automated, but there are preconditions for the distribution of the difference signals in the SERD spectra so that this method is not universally applicable. Moreover, this method results in the formation of artifacts, too.

Zhao et al. describe several integral transformations for the reconstruction of spectra, said transformations being based on the deconvolution of the SERD spectrum (J. Zhao, M. Carrabba, and F. Allen, Applied Spectroscopy, vol. 56, no. 7, 2002). These transformations can be automated, but the resulting reconstruction spectra are not free from artifacts, either.

Rebecca Willett describes the reconstruction problem as an inverse Poisson problem and uses a statistical expectation-maximization algorithm (Multiscale reconstruction for photon-limited shifted excitation Raman spectroscopy," ICASSP 2007). However, the used algorithm is not fully formulated, and there are some unanswered questions with respect to experimental realization regarding the selection of and the number of excitation frequencies.

The known algorithms for spectrum reconstruction provide purely qualitative spectra, and they result in the formation of artifacts or require previous knowledge of the Raman spectrum or preconditions for the SERD spectra so that automated and, at the same time, qualitative and quantitative SERD spectroscopy (e.g., concentration measurement series) is not possible according to the prior art.

It is therefore the object of the present invention to provide a method and a device for generating and for detecting a Raman spectrum that enable automated or automatable and, at the same time, qualitative and quantitative SERD spectroscopy (e.g., concentration measurement series).

SUMMARY

The inventive method for generating and for detecting a Raman spectrum of a medium to be analyzed has the following procedure steps: exposing the medium to be analyzed to excitation radiation, wherein the medium to be analyzed is exposed in a time-shifted manner to a first excitation radiation having a first wavelength and to a second excitation radiation having a second wavelength, wherein the first wavelength differs from the second wavelength; spectral analysis of the first excitation radiation scattered by the medium to be analyzed, wherein a first spectrum that assigns one intensity value each to a plurality of wavelengths is detected from the scattered first excitation radiation; spectral analysis of the second excitation radiation scattered by the medium to be analyzed, wherein a second spectrum that assigns one intensity value each to a plurality of wavelengths is detected from the scattered second excitation radiation; calculating a Raman spectrum of the medium to be analyzed from the first spectrum and the second spectrum, wherein the first spectrum and the second spectrum are normalized to each other with respect to their intensity values, and subsequently a first difference spectrum is calculated from the difference between the first spectrum and the second spectrum, a second difference spectrum is calculated from the difference between the second spectrum and the first spectrum, the first difference spectrum is converted into a first transformation spectrum, wherein one intensity value each is assigned to a plurality of wavelengths, and the intensity value of a wavelength of the first transformation spectrum is calculated by adding a first intensity value of a first wavelength of the first difference spectrum and the amount of a second intensity value of a second wavelength of the first difference spectrum, wherein the first wavelength of the first difference spectrum is greater than the wavelength of the first transformation spectrum by a predetermined transformation parameter and the second wavelength of the first difference spectrum is smaller than the wavelength of the first transformation spectrum by the transformation parameter, and the second difference spectrum is converted into a second transformation spectrum, wherein one intensity value each is assigned to a plurality of wavelengths, and the intensity value of a wavelength of the second transformation spectrum is calculated by adding the amount of a first intensity value of a first wavelength of the second difference spectrum and a second intensity value of a second wavelength of the second difference spectrum, wherein the first wavelength of the second difference spectrum is greater than the wavelength of the second transformation spectrum by the transformation parameter and the second wavelength of the second difference spectrum is smaller than the wavelength of the second transformation spectrum by the transformation parameter, and the Raman spectrum is calculated by adding the first transformation spectrum and the second transformation spectrum.

If the arrangement of measuring instruments is calibrated to one of the two initial spectra (first spectrum or second spectrum) before the measurement, the wavenumber scale is preferably shifted after the calculation of the Raman spectrum (adding the first transformation spectrum and the second transformation spectrum) by + or −Delta/2 (i.e., by half the wavelength spacing) depending on which of the two original spectra the arrangement of measuring instruments was calibrated to.

Preferably, half the amount of the difference between the first wavelength and the second wavelength is used as a transformation parameter. The first wavelength and the second wavelength are preferably selected from the 250-1100 nm interval, very preferably from the 400-950 nm interval.

The concept of the present invention comprises using a novel reconstruction algorithm for automated shifted-excitation Raman difference spectroscopy (SERDS) for on-line and in-situ applications. As against the prior art, the method is characterized by the fact that it can be easily automated, i.e., without having any information about the sample (medium to be analyzed) in advance and without any interventions by an operator. It has been found that the quantitative information of the spectra is preserved when the inventive method is used. Furthermore, the inventive method is universally suitable for all Raman apparatuses that allow multiple-wavelength excitation, and it can also be used for other spectroscopic methods, e.g., IR absorption, atomic fluorescence for background suppression, for the reconstruction of conventional Raman derivative spectra, or generally for the reconstruction of derivative spectra.

Figure 7:
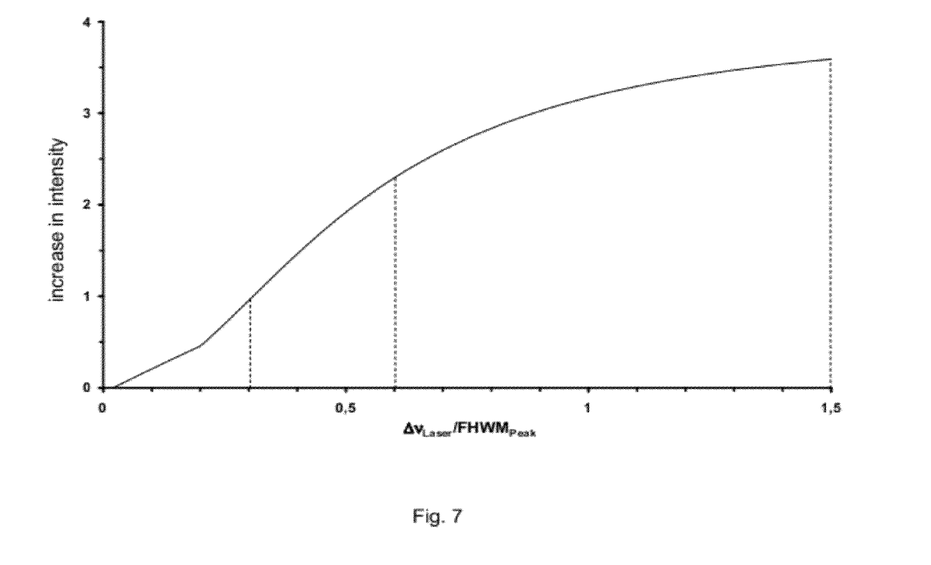
FIG. 7 shows the operative range of the method plotted as the signal intensity over the quotient of $\Delta v_{Laser}/FWHM_{Peak}$.

The spacing between the two wavelengths may have almost any value. Preferably, the wavelength spacing value $\Delta$ is selected to be $\geq$FWHM/2; preferred intervals for the ratio $\Delta v_{Laser}$/FWHM$_{Peak}$ are 0.3-10, very preferably 0.6-1.5. FIG. 7 shows the operative range of the method. It has been found that the operative range is between 0.6 and 1.5 for the quotient of the wavelength shift and the full width at half maximum $\Delta v_{Laser}$/FWHM$_{Peak}$.

Figure 6:
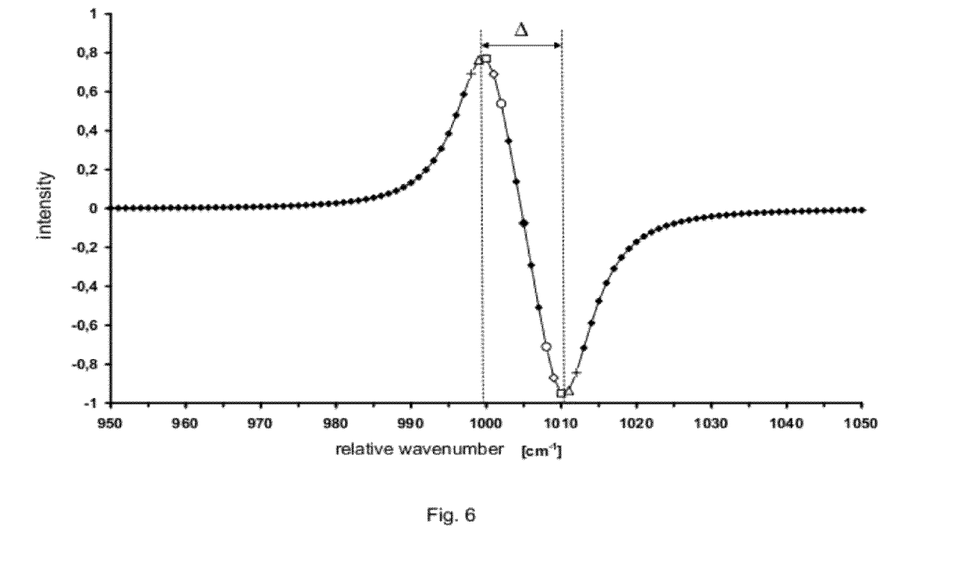
FIG. 6 shows the representation of further points suitable for reconstruction for the purpose of repeated application (pairs of points are marked by symbols)

Another advantage over the prior-art reconstruction methods includes the possibility of applying the reconstruction method repeatedly. By varying the transformation parameter $\delta$, n further spectra can be constructed from the same raw data and added afterwards, which is approximately equivalent to n individual SERDS measurements when the method is applied n times. The noise decreases by a factor of $\sqrt{n}$ when the method is applied n times, and the signal increases by a factor of n in the first approximation. The number of applications of the algorithm may be increased until the signal-to-background ratio cannot be improved any more, wherein the number of repetitions is limited by the number of the data points in the range of the extrema of the difference peak (see FIG. 6). The number of repetitions n cannot be higher than the number of pixels k in the range of the full width at half maximum FWHM of the Raman signal. Since repetitions in the range of small difference intensities do not result in an improvement of the SERDS intensity any more, the number of the repetitions of the application of the algorithm n is preferably selected to be between 1 and k/2. When the algorithm is applied repeatedly, the transformation parameter $\delta$ is preferably varied in even-numbered steps by up to +/−k/4 pixels starting from half the wavelength spacing $\Delta_{Laser}$.

The inventive method for generating and for detecting a Raman spectrum of a medium to be analyzed has the following procedure steps: exposing the medium to be analyzed to excitation radiation, wherein the medium to be analyzed is exposed in a time-shifted manner to a first excitation radiation having a first wavelength and to a second excitation radiation having a second wavelength, wherein the first wavelength differs from the second wavelength; spectral analysis of the first excitation radiation scattered by the medium to be analyzed, wherein a first spectrum that assigns one intensity value each to a plurality of wavelengths is detected from the scattered first excitation radiation; spectral analysis of the second excitation radiation scattered by the medium to be analyzed, wherein a second spectrum that assigns one intensity value each to a plurality of wavelengths is detected from the scattered second excitation radiation; calculating a Raman spectrum of the medium to be analyzed from the first spectrum and the second spectrum, wherein the first spectrum and the second spectrum are normalized to each other with respect to their intensity values, and subsequently a first difference spectrum is calculated from the difference between the first spectrum and the second spectrum, a second difference spectrum is calculated from the difference between the second spectrum and the first spectrum, the first difference spectrum is converted into a first transformation spectrum, wherein one intensity value each is assigned to a plurality of wavelengths, and the intensity value of a wavelength of the first transformation spectrum is calculated by adding a first intensity value of a first wavelength of the first difference spectrum and the amount of a second intensity value of a second wavelength of the first difference spectrum, wherein the first wavelength of the first difference spectrum is greater than the wavelength of the first transformation spectrum by a predetermined transformation parameter and the second wavelength of the first difference spectrum is smaller than the wavelength of the first transformation spectrum by the transformation parameter, the second difference spectrum is converted into a second transformation spectrum, wherein one intensity value each is assigned to a plurality of wavelengths, and the intensity value of a wavelength of the second transformation spectrum is calculated by adding the amount of a first intensity value of a first wavelength of the second difference spectrum and a second intensity value of a second wavelength of the second difference spectrum, wherein the first wavelength of the second difference spectrum is greater than the wavelength of the second transformation spectrum by the transformation parameter and the second wavelength of the second difference spectrum is smaller than the wavelength of the second transformation spectrum by the transformation parameter, and the Raman spectrum is calculated by adding the first transformation spectrum and the second transformation spectrum.

Preferably, half the amount of the difference between the first wavelength and the second wavelength is used as a transformation parameter. The first wavelength and the second wavelength are preferably selected from the 250-1100 nm interval, preferably from the 400-950 nm interval. Electromagnetic excitation radiation is preferably generated by means of a laser diode with an internal frequency-selective element. For generating varying excitation wavelengths in an alternating manner, the laser diode is preferably driven with two different excitation conditions in an alternating manner by means of the electric current applied to the laser diode. Preferably, toggling between the excitation conditions is performed at a frequency that is higher than 1 Hz. Preferably, the spectral analysis of the electromagnetic radiation scattered by the medium to be analyzed is performed by coupling the scattered radiation into a spectro-optical apparatus. Preferably, the detection of the individual Raman spectra that have varying excitation wavelengths is synchronized with the alternating driving of the laser diode. The detection of a Raman spectrum is preferably performed in each case within a time interval in which the amperage of the current that is applied to the laser diode is kept constant.

Preferably, the laser diode is driven with at least two different excitation conditions within a time interval in such a manner that it emits at at least two wavelengths with a wavelength spacing that corresponds to at least a third of the full width at half maximum of the Raman signals (more preferably to half the full width at half maximum, and very preferably to the full width at half maximum). Preferably, the laser diode is driven with at least two different excitation conditions within a time interval in such a manner that it emits at at least two wavelengths with a wavelength spacing that corresponds to at least 3 $cm^{-1}$ (0.2 nm when excited at 785 nm), more preferably to at least 4 $cm^{-1}$, and even more preferably to at least 8 $cm^{-1}$.

Preferably, the time interval is 1 s, more preferably 0.1 s. Preferably, the laser diode is calibrated before the excitation radiation is coupled into the medium to be analyzed. Preferably, a grating, an etalon or a Mach-Zehnder interferometer is used as a frequency-selective element. Preferably, the excitation radiation generated by the laser diode is coupled into the medium to be analyzed by means of a Raman measuring head. Preferably, the excitation radiation generated by the laser diode is amplified before it is coupled into the medium to be analyzed. Preferably, the radiation scattered by the medium to be analyzed is coupled into the spectro-optical system by means of an optical fiber. Preferably, the laser diode is driven by means of a power source, wherein the output power of the power source is modulated. Preferably, a function generator is used for modulation. Preferably, the individual Raman spectra are stored by means of a data processing device. Preferably, both a modulation of the output power of an excitation source and a synchronization of a detector of the spectro-optical system are carried out for synchronizing the detections of the Raman spectra with the driving of the laser diode.

The inventive device for generating an excitation radiation and for detecting a Raman spectrum of a medium to be analyzed has an excitation light source, means for coupling the excitation radiation emitted by the excitation light source into the medium to be analyzed, means for coupling the radiation scattered by the medium to be analyzed into a spectro-optical system, and a data processing device that is connected to the spectro-optical system, wherein the data processing device calculates a Raman spectrum of the medium to be analyzed from the at least two detected Raman spectra that have varying excitation wavelengths, in which calculated Raman spectrum the fluorescence background has been eliminated by way of calculation, and wherein the data processing device is designed to normalize the first spectrum and the second spectrum to each other with respect to their intensity values, and subsequently a first difference spectrum is calculated from the difference between the first spectrum and the second spectrum, a second difference spectrum is calculated from the difference between the second spectrum and the first spectrum, the first difference spectrum is converted into a first transformation spectrum, wherein one intensity value each is assigned to a plurality of wavelengths, and the intensity value of a wavelength of the first transformation spectrum is calculated by adding a first intensity value of a first wavelength of the first difference spectrum and the amount of a second intensity value of a second wavelength of the first difference spectrum, wherein the first wavelength of the first difference spectrum is greater than the wavelength of the first transformation spectrum by a predetermined transformation parameter and the second wavelength of the first difference spectrum is smaller than the wavelength of the first transformation spectrum by the transformation parameter, and the second difference spectrum is converted into a second transformation spectrum, wherein one intensity value each is assigned to a plurality of wavelengths, and the intensity value of a wavelength of the second transformation spectrum is calculated by adding the amount of a first intensity value of a first wavelength of the second difference spectrum and a second intensity value of a second wavelength of the second difference spectrum, wherein the first wavelength of the second difference spectrum is greater than the wavelength of the second transformation spectrum by the transformation parameter and the second wavelength of the second difference spectrum is smaller than the wavelength of the second transformation spectrum by the transformation parameter, and the Raman spectrum is calculated by adding the first transformation spectrum and the second transformation spectrum.

Preferably, half the amount of the difference between the first wavelength and the second wavelength is used as a transformation parameter. Preferably, the excitation light source is a laser diode with an internal frequency-selective element. For generating varying excitation wavelengths, the laser diode is preferably connected to a power source modulated by a modulator, wherein the modulator modulates the power source in an alternating manner. Preferably, toggling is performed at a frequency that is higher than 1 Hz. Preferably, the spectro-optical system is a spectrograph with a CCD detector. Preferably, the spectro-optical system and/or the data processing device are/is connected to the modulator, and the detection of the individual Raman spectra that have varying excitation wavelengths is synchronized with the alternating driving of the laser diode. Preferably, the modulator is a function generator. Preferably, the modulator is a square-wave generator. Preferably, the means for coupling the excitation radiation into the medium to be analyzed and the means for coupling the radiation scattered by the medium to be analyzed into the spectro-optical system have an optical fiber and a Raman measuring head. Preferably, an optical amplifier is arranged between the laser diode and the medium to be analyzed. Preferably, the internal frequency-selective element is a grating, an etalon, or a Mach-Zehnder interferometer.

BRIEF DESCRIPTION OF THE DRAWINGS

In the following, the invention will be explained in greater detail on the basis of the figures in which.

DETAILED DESCRIPTION

Figure 1:
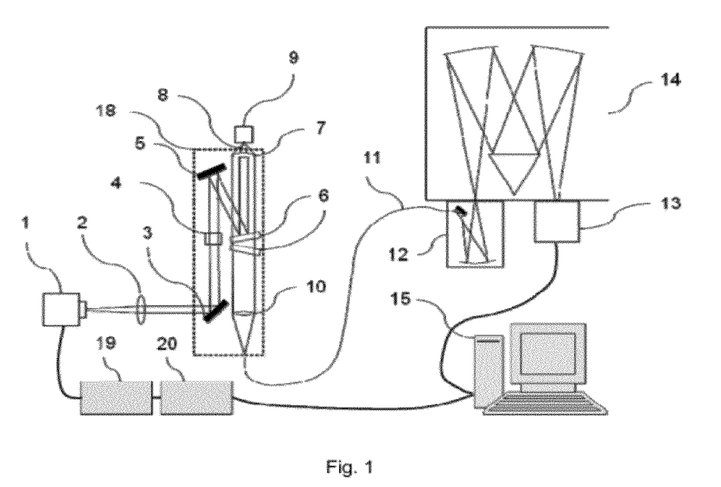
FIG. 1 shows a device for generating an excitation radiation and for detecting a Raman spectrum, according to a preferred embodiment of the invention.
Figure 2:
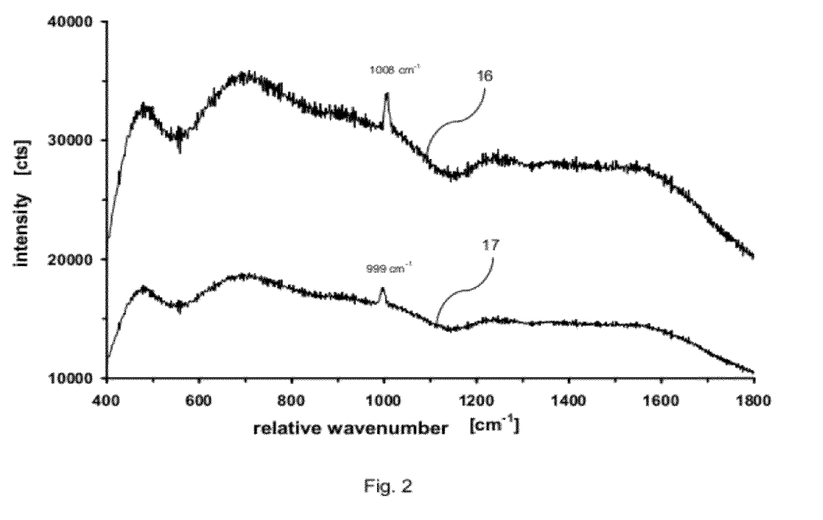
FIG. 2 shows two measured Raman spectra that are shifted with respect to each other on account of their varying excitation wavelengths.

The difference between the recording of SERD spectra and conventional Raman measurements comprises carrying out two measurements of the same sample 9 with two excitation wavelengths λ1 and λ2 instead of carrying out a single measurement, said two excitation wavelengths λ1 and λ2 being shifted with respect to each other by a wavelength difference Δ. The arrangement shown in FIG. 1 is used for the measurements. The DFB diode laser 1 is successively driven with two different injection currents, whereby the Raman signals of the two spectra are shifted with respect to each other corresponding to Δ, whereas the broadband background is not changed in the first approximation (FIG. 2). The intensities of the two spectra 16 and 17 differ from each other because the power of the laser depends on the set amperage.

Figure 3:
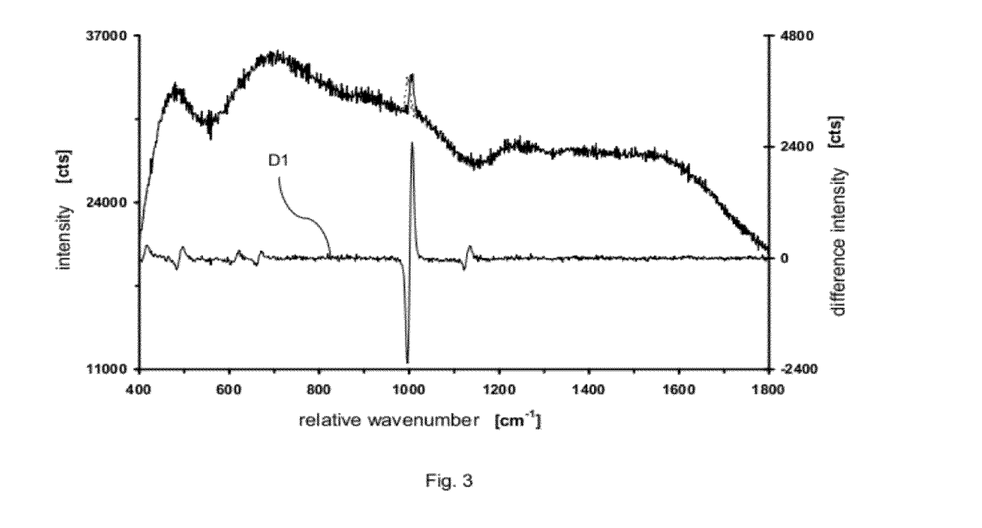
FIG. 3 shows the Raman spectra measured in FIG. 2, after their normalization to each other with respect to their intensities, and also shows a difference spectrum formed therefrom afterwards.
Figure 4:
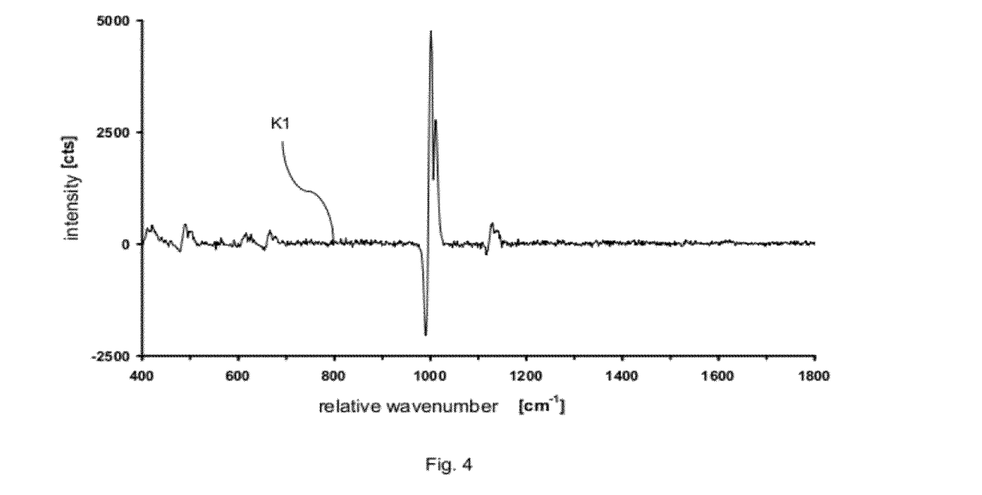
FIG. 4 shows a transformation spectrum obtained from the difference spectrum shown in FIG. 3 by means of the inventive method.
Figure 5:
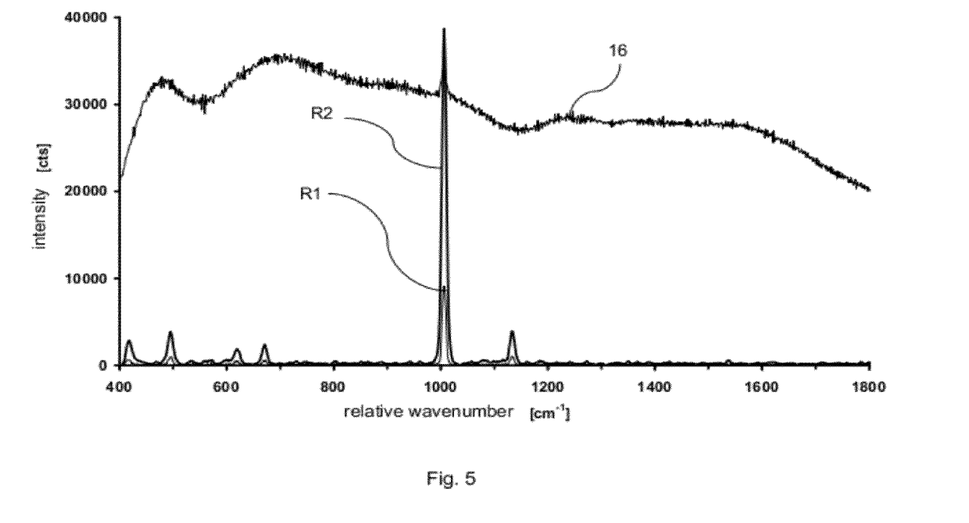
FIG. 5 shows two Raman spectra reconstructed from the Raman spectra measured in FIG. 2, in comparison with a conventionally measured Raman spectrum of calcium sulfate, which reconstruction was performed by means of the inventive method and which reconstructed Raman spectra were determined from the same data after single and fivefold reconstruction, respectively.

The two Raman spectra 16 and 17 are then normalized to each other with respect to their intensities, and the difference is formed (FIG. 3). The resulting difference spectrum D1 is first converted into the transformation spectrum K1 by means of the inventive reconstruction algorithm (FIG. 4), and the Raman spectrum R1 is reconstructed from the transformation spectrum K1 by adding K1 and K2 (FIG. 5).

Another advantage over the prior-art reconstruction methods includes the possibility of applying the reconstruction method repeatedly.

According to the present invention, repeated application of the reconstruction method means that the steps of
  converting the first difference spectrum D1 into a first transformation spectrum K1, wherein one intensity value each is assigned to a plurality of wavelengths, and the intensity value of a wavelength of the first transformation spectrum K1 is calculated by adding a first intensity value of a first wavelength of the first difference spectrum D1 and the amount of a second intensity value of a second wavelength of the first difference spectrum D1, wherein the first wavelength of the first difference spectrum D1 is greater than the wavelength of the first transformation spectrum K1 by a predetermined transformation parameter δ and the second wavelength of the first difference spectrum D1 is smaller than the wavelength of the first transformation spectrum K1 by the transformation parameter δ, and
  converting the second difference spectrum D2 into a second transformation spectrum K2, wherein one intensity value each is assigned to a plurality of wavelengths, and the intensity value of a wavelength of the second transformation spectrum K2 is calculated by adding the amount of a first intensity value of a first wavelength of the second difference spectrum D2 and a second intensity value of a second wavelength of the second difference spectrum D2, wherein the first wavelength of the second difference spectrum D2 is greater than the wavelength of the second transformation spectrum K2 by the transformation parameter δ and the second wavelength of the second difference spectrum D2 is smaller than the wavelength of the second transformation spectrum K2 by the transformation parameter δ,
are performed repeatedly, wherein the process of repeated application includes varying the transformation parameter δ between 0.2 Δ and 0.8 Δ and the plurality of transformation spectra K1, K2 obtained in this manner are added up.

By varying the increment δ (preferably, δ=Δ/2 if n=1), n further spectra can be constructed from the same raw data and added afterwards, which is approximately equivalent to n individual SERDS measurements when the method is applied n times. The noise decreases by a factor of √n when the method is applied n times, and the signal increases by a factor of n in the first approximation. The number of applications of the algorithm may be increased until the signal-to-background ratio cannot be improved any more, wherein the number of repetitions is limited by the number of the data points in the range of the extrema of the difference peak (see FIG. 6). The number of repetitions cannot be higher than the number of pixels k in the range of the full width at half maximum FWHM of the Raman signal. Since repetitions in the range of small difference intensities do not result in an improvement of the SERDS intensity any more, the number of the repetitions of the application of the transformation n is preferably selected to be between 1 and k/2. When the algorithm is applied repeatedly, the spacing δ is preferably varied in even-numbered steps by up to +/−k/4 pixels starting from half the wavelength spacing $\Delta_{Laser}$.

A significantly improved reconstructed Raman spectrum R2 may be obtained by fivefold application of the reconstruction method (FIG. 5).

Figure 8:
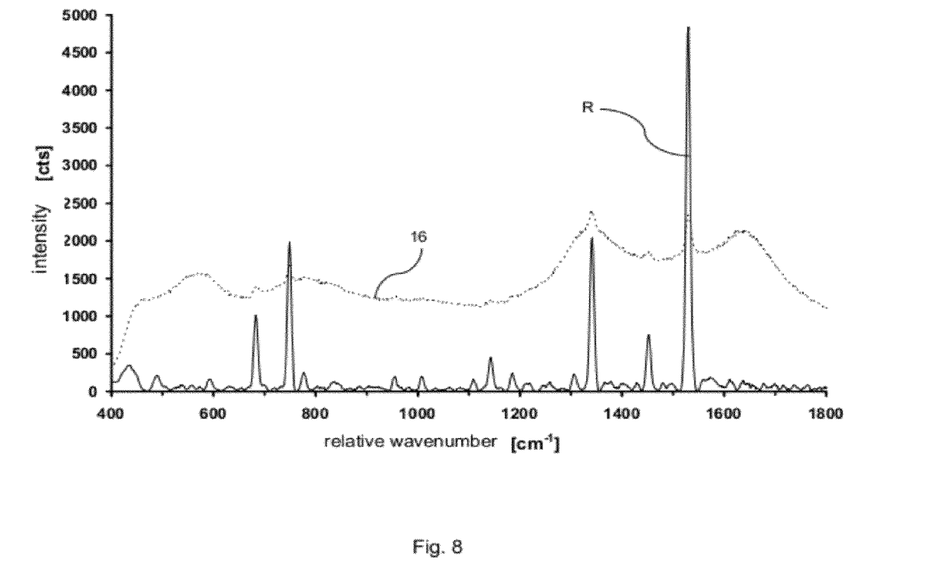
FIG. 8 shows a conventionally measured Raman spectrum and a Raman spectrum determined by means of the inventive method of 100 μM of copper(II) phthalocyanine-tetrasulfonic acid tetrasodium salt in distilled water.
Figure 9:
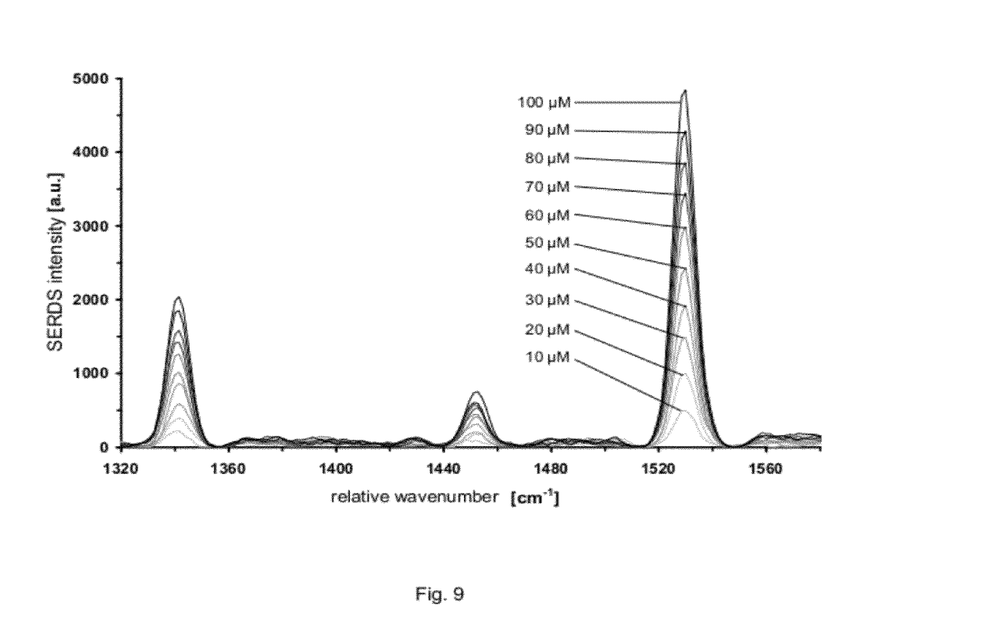
FIG. 9 shows various Raman spectra of copper(II) phthalocyanine-tetrasulfonic acid tetrasodium salt of varying concentrations in distilled water, which Raman spectra were determined by means of the inventive method.
Figure 10:
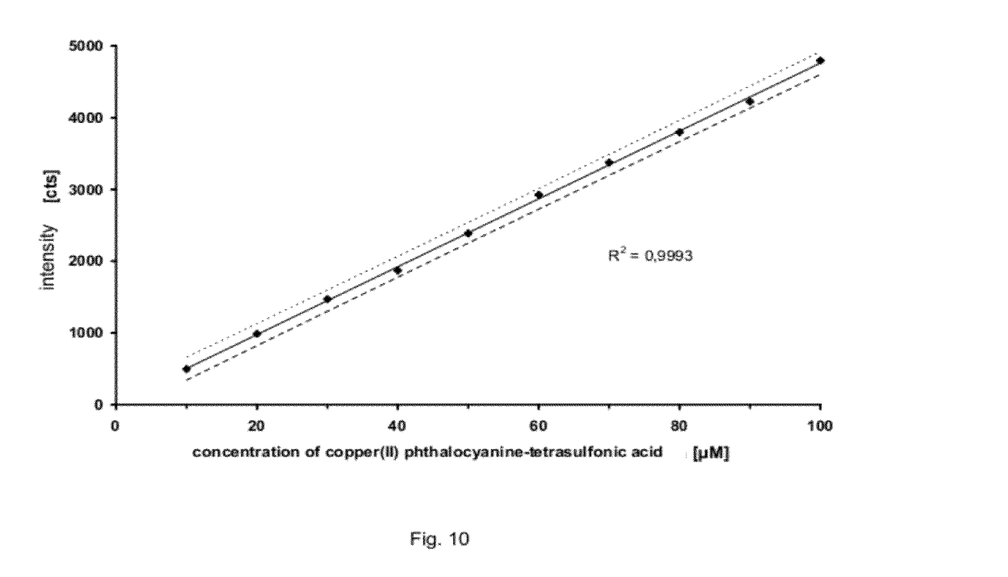
FIG. 10 shows the calibration curve for the Raman signal at 1530 $cm^{-1}$ of FIG. 9.

FIG. 8 to FIG. 10 show the quantitative evaluation of a concentration measurement series (conventionally and by means of SERDS) illustrated by copper(II) phthalocyanine-tetrasulfonic acid tetrasodium salt in water.

The inventive evaluation method was first tested on a test object (highly scattering blackboard chalk), wherein the signal/background-noise ratio $S/\sigma_{BGN}$ was improved by a factor of 48. The positions and the relative intensities of the signals are preserved and enable the selectivity of qualitative assignment in the SERD spectrum reconstructed according to the invention to be higher than the selectivity of qualitative assignment in the conventional Raman spectrum because the FWHM values of the signals are reduced by the algorithm from observed 12 cm$^{-1}$ to 9.5 cm$^{-1}$. In the SERD spectra, all weak Raman signals that are masked in the conventional chalk spectrum by the background were found in the positions that are known from a gypsum crystal spectrum.

The quantitative evaluability of the SERDS measurements was demonstrated by recording a calibration curve of copper (II) phthalocyanine-tetrasulfonic acid tetrasodium salt in distilled water. The calibration curve was linear, and the detection limit for the SERDS measurement series (3 µM) was lower than the detection limit for the Raman measurement series (3.4 µM), wherein the limiting factor rather includes the inaccuracy that occurs when the solution is mixed, which limiting factor enters into the calculation of the detection limit.

The fact that the novel evaluation algorithm makes SERDS suitable for qualitative and quantitative measurements has been successfully demonstrated. The quality of the SERD spectra was always significantly better than the quality of the conventionally recorded Raman spectra. The novel reconstruction algorithm enables on-line chemical analysis to be automated and totally user-independent for the first time. Almost any Raman system could be easily and cheaply adapted for the use of SERDS. Moreover, the developed technique is very well suitable for the mobile use of miniaturized Raman systems, e.g., in process control. The free choice of excitation wavelengths enables sensitivity to be adapted for any field of application. Moreover, SERDS may be used in combination with other Raman techniques (e.g., SERS and resonance Raman spectroscopy) as a matter of principle.

LIST OF REFERENCE NUMERALS 1 laser diode
2 first lens
3 first mirror
4 band-pass filter
5 second mirror
6 Raman filter (edge filter or notch filter)
7 second lens
8 excitation radiation
9 medium to be analyzed/sample (in a vessel)
10 third lens
11 optical fiber
12 spectro-optical system
13 CCD detector
14 spectrograph
15 data processing device
16 measured Raman spectrum at excitation wavelength $\lambda_1$
17 measured Raman spectrum at excitation wavelength $\lambda_2$
18 Raman measuring head
19 power supply
20 function generator
D1 first difference spectrum from 16 and 17
D2 second difference spectrum from 17 and 16
K1 first transformation spectrum
K2 second transformation spectrum
R, R1 Raman spectrum reconstructed according to the invention
R2 Raman spectrum reconstructed according to the invention, after fivefold application
Δ wavelength difference
δ transformation parameter

What is claimed is:

1. A method for generating and for detecting a Raman spectrum of a medium to be analyzed having the following procedure steps:
    exposing the medium to be analyzed to excitation radiation, wherein the medium to be analyzed is exposed in a time-shifted manner to a first excitation radiation having a first wavelength and to a second excitation radiation having a second wavelength, wherein the first wavelength differs from the second wavelength,
    spectral analysis of the first excitation radiation scattered by the medium to be analyzed, wherein a first spectrum that assigns one intensity value each to a plurality of wavelengths is detected from the scattered first excitation radiation,
    spectral analysis of the second excitation radiation scattered by the medium to be analyzed, wherein a second spectrum that assigns one intensity value each to a plurality of wavelengths is detected from the scattered second excitation radiation,
    calculating a Raman spectrum of the medium to be analyzed from the first spectrum and the second spectrum,
    wherein
    the first spectrum and the second spectrum are normalized to each other with respect to their intensity values, and subsequently:
    a) a first difference spectrum is calculated from the difference between the first spectrum and the second spectrum,
    b) a second difference spectrum is calculated from the difference between the second spectrum and the first spectrum,
    c) the first difference spectrum is converted into a first transformation spectrum, wherein one intensity value each is assigned to a plurality of wavelengths, and the intensity value of a wavelength of the first transformation spectrum is calculated by adding a first intensity value of a first wavelength of the first difference spectrum and the amount of a second intensity value of a second wavelength of the first difference spectrum, wherein the first wavelength of the first difference spectrum is greater than the wavelength of the first transformation spectrum by a predetermined transformation parameter and the second wavelength of the first difference spectrum is smaller than the wavelength of the first transformation spectrum by the transformation parameter,
    d) the second difference spectrum is converted into a second transformation spectrum, wherein one intensity value each is assigned to a plurality of wavelengths, and the intensity value of a wavelength of the second transformation spectrum is calculated by adding the amount of a first intensity value of a first wavelength of the second difference spectrum and a second intensity value of a second wavelength of the second difference spectrum, wherein the first wavelength of the second difference spectrum is greater than the wavelength of the second transformation spectrum by the transformation parameter and the second wavelength of the second difference spectrum is smaller than the wavelength of the second transformation spectrum by the transformation parameter, and e) the Raman spectrum is calculated by adding the first transformation spectrum and the second transformation spectrum.

2. The method of claim 1, wherein
a value of between 0.2 and 0.8 of the amount of the difference between the first wavelength and the second wavelength is used as a transformation parameter.

3. The method of claim 2, wherein
a value of between 0.4 and 0.6 of the amount of the difference between the first wavelength and the second wavelength is used as a transformation parameter.

4. The method of claim 3, wherein
half the amount of the difference between the first wavelength and the second wavelength is used as a transformation parameter.

5. The method of claim 4, wherein
steps c) and d) are repeated several times before step e) is performed, wherein the transformation parameter is varied with each repetition of steps c) and d), whereby a plurality of first transformation spectra and a plurality of corresponding second transformation spectra are obtained, wherein the Raman spectrum is calculated by adding the first transformation spectra and the second transformation spectra in step e).

6. The method of claim 5, wherein
the transformation parameter is increased or decreased with each repetition of steps c) and d).

7. The method of claim 6, wherein
half the amount of the difference between the first wavelength and the second wavelength is used as a transformation parameter when steps c) and d) are performed for the first time, and the transformation parameter is subsequently varied within the interval of 0.2 to 0.8 of the amount of the difference between the first wavelength and the second wavelength.

8. The method of claim 1, wherein
electromagnetic excitation radiation is generated by means of a laser diode with an internal frequency-selective element.

9. The Method of claim 8, wherein,
for generating varying excitation wavelengths in an alternating manner, the laser diode is driven with two different excitation conditions in an alternating manner by means of the electric current applied to the laser diode.

10. The method of claim 9, wherein
toggling between the excitation conditions is performed at a frequency that is higher than 1 Hz.

11. A device for generating an excitation radiation and for detecting a Raman spectrum of a medium to be analyzed, comprising:
an excitation light source,
means for coupling the excitation radiation emitted by the excitation light source into the medium to be analyzed,
means for coupling the radiation scattered by the medium to be analyzed into a spectro-optical system,
a data processing device that is connected to the spectro-optical system, wherein the data processing device calculates a Raman spectrum of the medium to be analyzed from the at least two detected Raman spectra that have varying excitation wavelengths, in which calculated Raman spectrum the fluorescence background has been eliminated by way of calculation, and
wherein
the data processing device is designed to normalize the first spectrum and the second spectrum to each other with respect to their intensity values, and subsequently:
a) a first difference spectrum is calculated from the difference between the first spectrum and the second spectrum,
b) a second difference spectrum is calculated from the difference between the second spectrum and the first spectrum,
c) the first difference spectrum is converted into a first transformation spectrum, wherein one intensity value each is assigned to a plurality of wavelengths, and the intensity value of a wavelength of the first transformation spectrum is calculated by adding a first intensity value of a first wavelength of the first difference spectrum and the amount of a second intensity value of a second wavelength of the first difference spectrum, wherein the first wavelength of the first difference spectrum is greater than the wavelength of the first transformation spectrum by a predetermined transformation parameter and the second wavelength of the first difference spectrum is smaller than the wavelength of the first transformation spectrum by the transformation parameter,
d) the second difference spectrum is converted into a second transformation spectrum, wherein one intensity value each is assigned to a plurality of wavelengths, and the intensity value of a wavelength of the second transformation spectrum is calculated by adding the amount of a first intensity value of a first wavelength of the second difference spectrum and a second intensity value of a second wavelength of the second difference spectrum, wherein the first wavelength of the second difference spectrum is greater than the wavelength of the second transformation spectrum by the transformation parameter and the second wavelength of the second difference spectrum is smaller than the wavelength of the second transformation spectrum by the transformation parameter, and
e) the Raman spectrum is calculated by adding the first transformation spectrum and the second transformation spectrum.

12. The device of claim 11, wherein the data processing device is designed in such a manner that a value of between 0.2 and 0.8 of the amount of the difference between the first wavelength and the second wavelength is used as a transformation parameter.

13. The device of claim 12, wherein
the data processing device is designed in such a manner that a value of between 0.4 and 0.6 of the amount of the difference between the first wavelength and the second wavelength is used as a transformation parameter.

14. The device of claim 13, wherein
the data processing device is designed in such a manner that half the amount of the difference between the first wavelength and the second wavelength is used as a transformation parameter.

15. The device of claim 11, wherein
the data processing device is designed in such a manner that steps c) and d) are repeated several times before step e) is performed, wherein the transformation parameter is varied with each repetition of steps c) and d), whereby a plurality of first transformation spectra and a plurality of corresponding second transformation spectra are obtained, wherein the Raman spectrum is calculated by adding the obtained first transformation spectra and the obtained second transformation spectra in step e).

16. The device of claim 15, wherein
the data processing device is designed in such a manner that the transformation parameter is increased or decreased with each repetition of steps c) and d).

17. The device of claim 16, wherein
the data processing device is designed in such a manner that half the amount of the difference between the first wavelength and the second wavelength is used as a transformation parameter when steps c) and d) are performed for the first time, and the transformation parameter is subsequently varied within the interval of 0.2 to 0.8 of the amount of the difference between the first wavelength and the second wavelength.

18. The device of claim 11, wherein
the excitation light source is a laser diode with an internal frequency-selective element.

19. The device of claim 11, wherein
for generating varying excitation wavelengths, the laser diode is connected to a power source modulated by a modulator, wherein the modulator modulates the power source in an alternating manner.

20. The device of claim 19, wherein
toggling is performed at a frequency that is higher than 1 Hz.

21. The device of claim 11, wherein
the spectro-optical system is a spectrograph with a CCD detector.

22. The device of claim 11, wherein
the spectro-optical system and/or the data processing device are/is connected to the modulator, and the detection of the individual Raman spectra that have varying excitation wavelengths is synchronized with the alternating driving of the laser diode.

23. The device of claim 22, wherein
the modulator is a square-wave generator.

* * * * *